United States Patent [19]
Cuilleron

[11] Patent Number: 5,133,765
[45] Date of Patent: Jul. 28, 1992

[54] UNIT TO FIT A PROSTHESIS COMPONENT

[75] Inventor: Jean Cuilleron, Saint Etienne, France

[73] Assignee: Fabrique d'Implants et d'Instruments Chrirugicaux, Saint Just Malmont, France

[21] Appl. No.: 446,861

[22] Filed: Dec. 6, 1989

[30] Foreign Application Priority Data

Dec. 7, 1988 [FR] France .............................. 88 16501

[51] Int. Cl.⁵ .......................... A61F 2/32; B65D 85/58
[52] U.S. Cl. ....................................... 623/22; 206/363
[58] Field of Search ...................... 623/16, 18, 22, 23

[56] References Cited

U.S. PATENT DOCUMENTS

| | | | |
|---|---|---|---|
| 1,338,978 | 5/1920 | Davis | 101/405 |
| 4,542,825 | 9/1985 | Thomas et al. | 423/23 |
| 4,686,971 | 8/1987 | Harris et al. | 606/99 |
| 4,735,143 | 4/1988 | Weir | 101/405 |
| 4,865,609 | 9/1989 | Roche | 623/23 |

Primary Examiner—David Isabella
Attorney, Agent, or Firm—Eric P. Schellin

[57] ABSTRACT

The unit A to fit a femoral head T of the prosthesis component or element consisting of a body 1, one part of which is constructed to temporarily take the femoral head T, whereas another part has means to likely to eject the the femoral head T with a view to positioning it onto a complementary part Ta of the prothesis element.

6 Claims, 2 Drawing Sheets

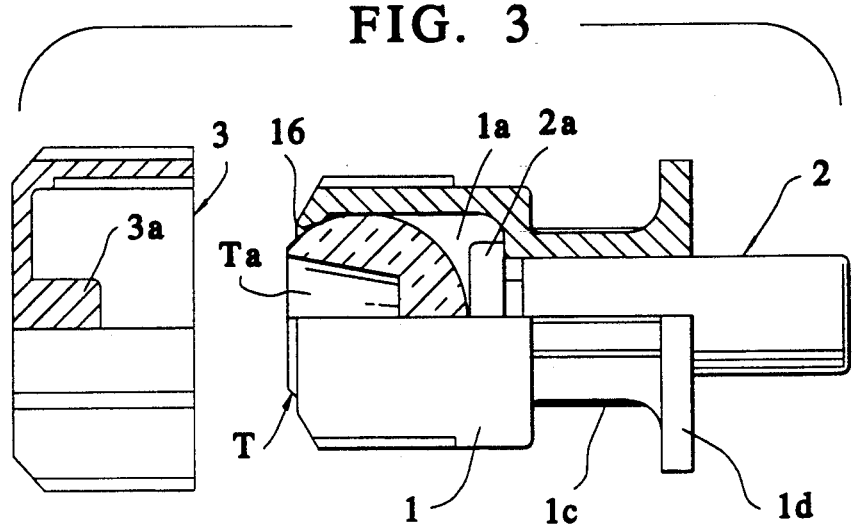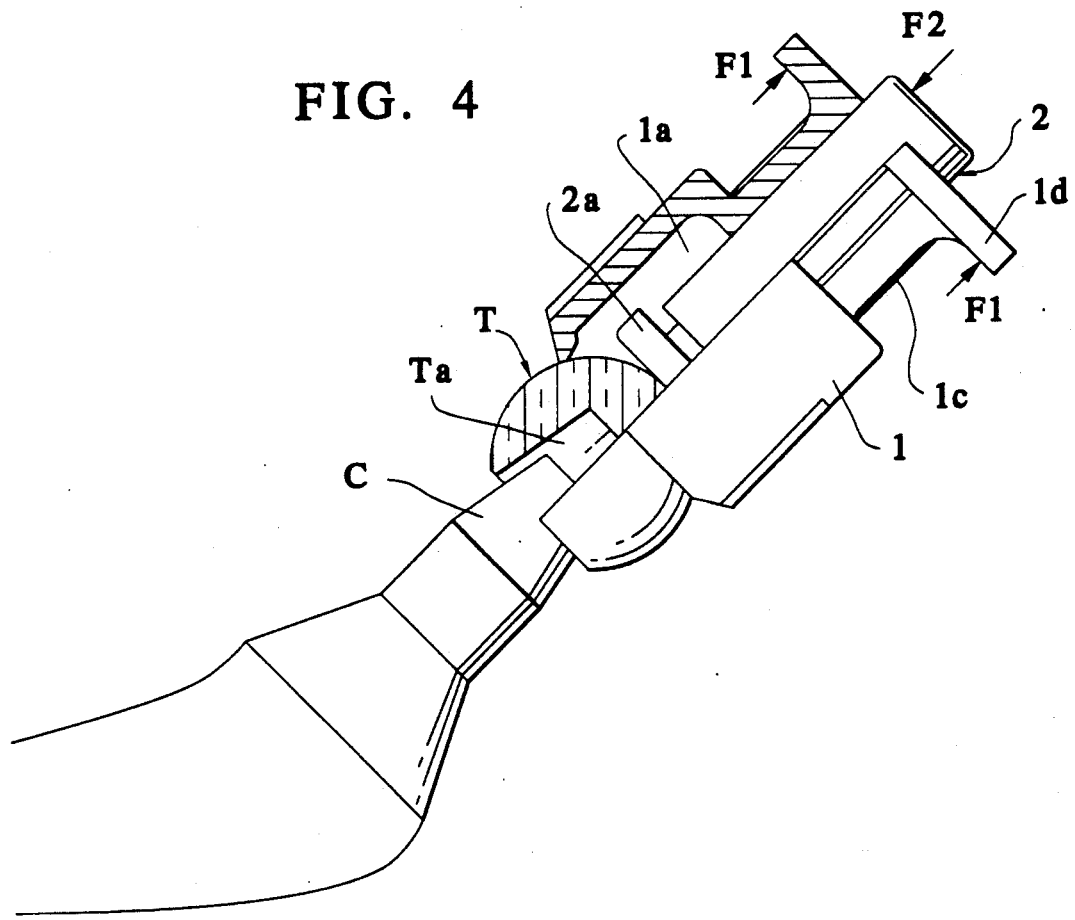

UNIT TO FIT A PROSTHESIS COMPONENT

BACKGROUND OF THE INVENTION

1. Field of the Invention

The invention relates to a unit A to fit a femoral head T prosthesis component or element, and more particularly, however not limitatively, to a unit A selectively fitting a femoral head T onto the corresponding part Ta of a hip prosthesis element.

The femoral shaft is positioned on the neck C of a stem provided for insertion into an internal complementary part Ta of a hip prothesis element by the practitioner during the surgical operation creates a lot of problems.

Spherical shape of the femoral heads makes it difficult for them to be handled. This difficulty is increased by the fact that the surgeon wears moist gloves, which are often covered with blood. Therefore, there are risks of slipping and consequently of dropping the head which may cause damage to the head.

If the surgeon was not to drop the head, this type of handling creates other disadvantages such as:

risk of damaging the surface finish of the head considering that stainless steel can be scratched very easily;

risk of introducing various impurities into the recess of the head which are likely to become trapped inside the head after it has been fitted onto the neck of the prosthesis; and difficulty in fitting the head onto the neck of the prosthesis which is already introduced into the medullary canal, emphasizing that the femoral head has to be swivelled for its recess to be in front of the neck.

Furthermore, it is understood that such handling operations strongly jeopardize the sterilization of the heads, despite all the precautions initially taken to provide perfect sterilization of the heads before they are to be positioned in place.

2. Description of the Prior Art

This type of implant is known, generally comprise a stem inserted into the centromedullary canal of the femur and a neck destined to take a spherical femoral head. In the majority of cases, this femoral head has a recess complementary to that of the neck of the stem. The recess of the head and the neck are very often tapered.

These known prior uses teach and disclose various types of prosthesis components of sorts and of various manufactures and the like as well as methods of their construction, but none of them whether taken singly or in combination disclose the specific details of the combination of the invention in such a way as to bear upon the claims of the present invention.

SUMMARY OF THE INVENTION

An object of the invention is aimed at overcoming these disadvantages in a simple and efficient manner by implementing a unit A to selectively fit the femoral head T, particularly those of prosthetic elements.

In order to overcome the problem of suppressing all direct handling operations with the head T, the unit A is constructed to comprise a body 1, one part of which is constructed in order to temporily take the femoral head T, whereas the other part has means likely to eject the femoral head T with a view to it being positioned on the complementary part Ta of the femoral head T.

The invention also endeavors to overcome the problem of being able to pre-position the head T inside the unit A before it is fitted onto the neck C of the femoral head T by acting as packaging for the head T, thereby adhering to conventional sterilization requirements.

Such a problem is overcome in that the part of the body 1 constructed to temporarily take the prosthesis element, cooperates so as to be removed with a plugging component or obturating member 3 likely to protect the femoral head T.

It is therefore possible to pack the whole unit A, which in this case, acts as both ancillary positioning and packaging for the spherical head T or another femoral head, in one or several priorly sterilized shells (not shown).

In order to overcome the problem of the prior art and to achieve a further object of the invention, and to provide for temporarily holding the femoral head T, the part of the body 1 taking the femoral head T is made up of an the internal chamber 1a constructed so as to temporarily position and hold the femoral head T whilst being capable of ejecting it under the effect of a force applied to the femoral head T.

In order to solve the problem defined and brought up above, i.e., to automatically fit the femoral head T without direct contact with the hands of an operator, an ejection member 2 made up as a pushbutton 2 freely slides into the body 1, one end of which is formed so as to cooperate by being applied against the femoral head T, the pushbutton 2 being operated in combination with the embodiments or ridges Ta of the body 1.

Another advantage of the invention is to provide embodiments of the body 1 made up of peripheral recesses or indentations 1c formed from generating lines and a support or holding collar 1d.

The problem brought up of pre-positioning the femoral head T of the prosthetic element in the unit A so that when it is assembled, it is in front of a corresponding complementary femoral head T of the prosthetic element is overcome in that the plugging component has an internal bearing surface likely to cooperate with a part of the femoral head T of the prosthetic element with a view to inserting it into the chamber of the body 1.

These together with other objects and advantages which will become subsequently apparent reside in the details of the process and operation thereof as more fully hereinafter is described and claimed, reference being had to the accompanying drawings forming a part hereof, wherein like numerals refer to like parts throughout.

DESCRIPTION OF THE SEVERAL VIEWS OF THE DRAWINGS

FIG. 3 is partial section and exploded view of the unit A and obturating member 3 and embodying concepts of the invention.

FIG. 4 is a partial section and assembled view of the unit A showing the manner in which the femoral head T of the prosthetic element is ejected from the unit A and embodying concepts of the invention.

DESCRIPTION OF A PREFERRED EMBODIMENT OF THE INVENTION

Figure 1:
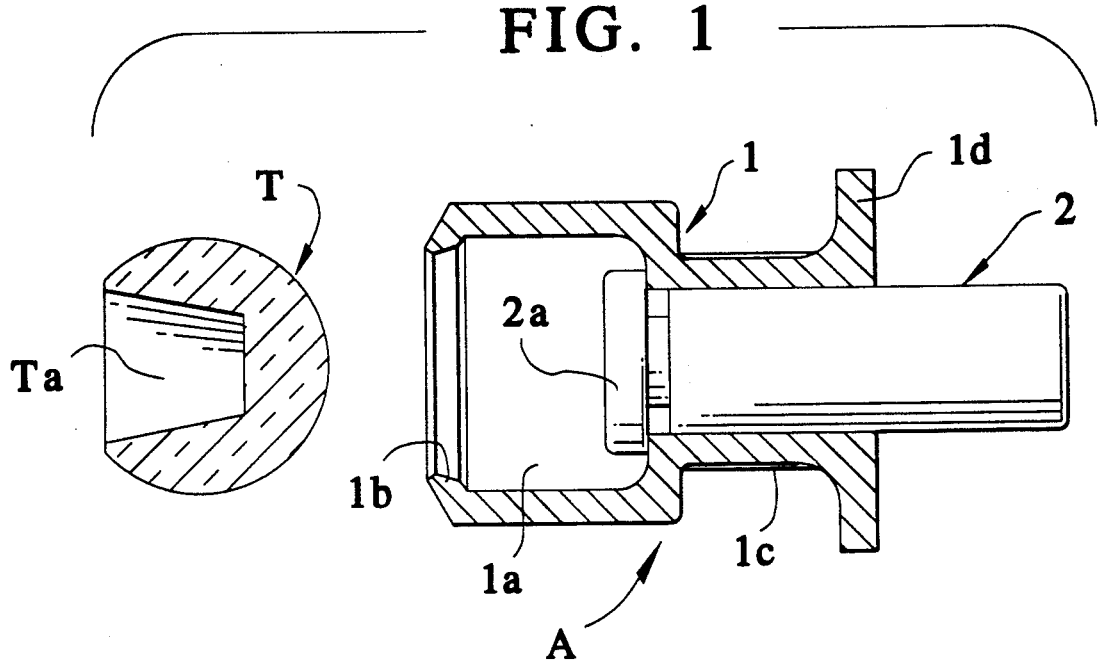
FIG. 1 is a partial section view of a unit A before a femoral head T of the prosthetic element is fitted thereto and illustrating a typical installation of the unit A according to a preferred embodiment and best mode of the present invention.

Referring now to the drawings there is shown in FIGS. 1-4 the application of the unit A relationally to fit a femoral head T on a neck C of a stem, as shown.

The unit A consists of a body prosthesis element 1 one part of which is likely to take the form of the spherical femoral head T. The body 1 of the unit A is of a generally cylindrical shape and has a internal chamber 1a to house the femoral head T.

An opening of this chamber 1a, in particularly, has either in a direct or built up manner, embodiment or ridge 1b formed to temporarily hold and retain the femoral head T, whilst enabling it to be ejected under the effect of a force applied to the femoral head T. For example, the open end of the chamber 1a may have a profiled retaining part, a boss or the like.

Axially of the chamber 1a the body 1 is fitted with a pushbutton 2 mounted tso as to freely slide. The end of this button 2 projects into the chamber 1a and has a flanged end 2a likely to be applied against the spherical femoral head T of the prosthetic element. The other end of the button 2 projects from the outside of the body 1 so as to be operated in combination with the embodiments of the body 1. For example, one part of the body 1 has peripheral recesses 1c formed from a line of generation and combined with a support collar 1d, to both grip the unit A with one hand and push the button 2, as is shown by the arrows in FIG. 4. If required or desired, the button 2 may be urged by elastic return means.

According to another important feature of the invention, the chamber 1a, the body 1 of the unit A takes so as to be removed, a plugging component 3 likely to protect the femoral head T housed in the chamber 1a.

This plugging component 3 can be made up of a cap 3 screwed onto the corresponding part of the body without this excluding any other dismantling mode of the fixing such as clipping, press fitting, and the like.

The bore of the cap 3 has an internal bearing surface 3a selectively to cooperate with the complementary part Ta which has originally been provided for the spherical femoral head T. These arrangements enable the femoral head T to be pre-positioned inside the unit A so that the complementary part Ta can be placed in front and in line with the neck C of the stem.

Figure 2:
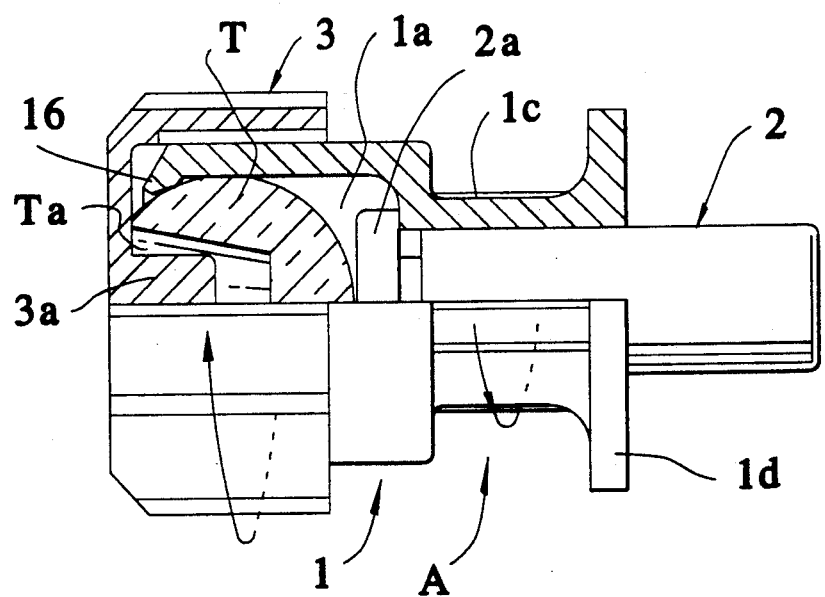
FIG. 2 is a partial section view of the unit A fitted with a plugging component or obturating member 3 and embodying concepts of the invention.

In an advantageous manner, in the form of an embodiment illustrated in FIG. 2, the whole unit A fitted with the cap 3 makes up packaging for the femoral head T and ancillary fitting of the femoral head T. Besides, the whole unit A can be packed in one or several suitably sterilized shells. This turns out to have a particularly advangateous use. For example, the surgeon's assistant, after having removed the unit A from the sterilization shells (not shown), removes the cap 3, FIG. 3, and gives the unit A fitted with the femoral head T to the surgeon. Then, the surgeon, who can perfectly and easily grip the unit A just has merely to put it in front of the neck C of the femoral head T. The complementary part Ta of the femoral head T of the prosthetic element being directly in line with the neck C, the forces F1 and F2 are applied to the pushbutton 2 and collar 1d, in order to provoke, under the thrust effect of the button 2, the election of the femoral head T which is positioned on the complementary part Ta of the neck C nearly automatically.

In summary the advantages are mde clearly apparent from the description and the following is concluded from the aspects of the invention:

fitting without direct contact with the head T which does not alter the sterilization; and saving in the time of the removal from the sterile packaging shells to the implantation onto the prosthesis.

The entire or whole unit A can be made from any materials and can be a disposable or re-useble component and the invention may be so constructed and arranged in its component parts that it may be assembled as a kit or in kit form.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to falling within the scope of the invention.

I claim:

1. Device for retaining and depositing a rounded femoral head of a prosthetic element comprising:

a substantially cylindrical body, said body having a first portion and axially therewith a second portion, said first portion having at one end a femoral head receiving outwardly extending axially disposed recess, said recess having a resiliently radially expandable axial opening, said opening having radially inwardly extending means whereby to frictionally engage said femoral head, said second portion having an axially disposed bore therethrough, said bore having an axially slidable plunger adapted and constructed to extend outwardly from said second portion when in one mode and to extend into said recess to abut against said femoral head to thereby eject said femoral head through said expandable opening when in a second mode to deposit said femoral head onto the prosthetic element.

2. The device of claim 1 wherein the second portion of the body has an outwardly extending annular recess thereabout.

3. The device of claim 1 wherein the first portion has a removable cup shaped cover to enclose said first portion.

4. The device of claim 3 wherein the second portion of the body has an outwardly extending annular recess thereabout.

5. The device of claim 3 wherein the removable cup shaped cover has a centrally located proturberance internally of said cup shaped cover adapted and constructed to abut against the femoral head when in position.

6. The device of claim 5 wherein the second portion of the body has an outwardly extending annular recess thereabout.

* * * * *